United States Patent
Stollberg et al.

(10) Patent No.: US 9,668,979 B2
(45) Date of Patent: Jun. 6, 2017

(54) PIPERAQUINE MICROCAPSULES AND COMPOSITIONS CONTAINING THEM

(71) Applicant: ADARE PHARMACEUTICALS S.R.L., Pessano Con Bornago (IT)

(72) Inventors: Christian Stollberg, Carugate (IT); Giancarla Bianchi, Lacchiarella (IT); Flavio Fabiani, Vimercate (IT); Luigi Boltri, Agrate Brianza (IT)

(73) Assignee: Adare Pharmaceuticals, Inc., Lawrenceville, NJ (US)

( * ) Notice: Subject to any disclaimer, the term of this patent is extended or adjusted under 35 U.S.C. 154(b) by 0 days.

(21) Appl. No.: 14/779,215

(22) PCT Filed: Mar. 21, 2014

(86) PCT No.: PCT/EP2014/055747
§ 371 (c)(1),
(2) Date: Sep. 22, 2015

(87) PCT Pub. No.: WO2014/147242
PCT Pub. Date: Sep. 25, 2014

(65) Prior Publication Data
US 2016/0045447 A1    Feb. 18, 2016

Related U.S. Application Data

(60) Provisional application No. 61/804,448, filed on Mar. 22, 2013.

(51) Int. Cl.
| | |
|---|---|
| A61K 9/16 | (2006.01) |
| A61K 9/50 | (2006.01) |
| A61K 31/496 | (2006.01) |
| A61K 45/06 | (2006.01) |
| A61K 9/00 | (2006.01) |

(52) U.S. Cl.
CPC .......... *A61K 9/5047* (2013.01); *A61K 9/5089* (2013.01); *A61K 31/496* (2013.01); *A61K 45/06* (2013.01); *A61K 9/0056* (2013.01)

(58) Field of Classification Search
None
See application file for complete search history.

(56) References Cited

U.S. PATENT DOCUMENTS

| | | | |
|---|---|---|---|
| 2005/0287219 A1* | 12/2005 | Murthy | A61K 31/165 424/488 |
| 2011/0250281 A1* | 10/2011 | Mapelli | A61K 9/5026 424/495 |
| 2012/0183607 A1* | 7/2012 | Enose | A61K 9/1652 424/452 |

OTHER PUBLICATIONS

Nimbalkar et al. (WO 2009050734).*
Shah, PP et al., Design and Optimization of Mefloquine Hydrochloride Microparticles for Bitter Taste Masking, AAPS PharmSciTech, Jun. 2008, 337-389, vol. 9 No. 2 (published online Feb. 20, 2009).
Ndesendo, VMK et al., Microencapsulation of chloroquine diphosphate by Eudragit RS100, Journal of Microencapsulation, Jan./Feb. 1996, 1-8, vol. 13 No. 1, Taylor and Francis, Basingstroke, GB.

* cited by examiner

*Primary Examiner* — Robert A Wax
*Assistant Examiner* — Quanglong Truong
(74) *Attorney, Agent, or Firm* — Cooley LLP

(57) ABSTRACT

The present invention provides a microcapsule pharmaceutical composition of at least a bisquinoline drug. said microcapsule comprises a drug core of a pharmaceutically effective amount of a bisquinoline drug and a polymeric coating over the core. This microcapsule pharmaceutical composition has desirable pharmaceutical properties, including taste masking effect and a high stability.

28 Claims, 7 Drawing Sheets

PIPERAQUINE MICROCAPSULES AND COMPOSITIONS CONTAINING THEM

REFERENCE TO PRIOR APPLICATION

This application claims the benefit of International Application No. PCT/EP2014/055757 and U.S. Provisional Application No. 61/804,448, filed Mar. 22, 2013, the disclosure of each of which is incorporated by reference herein in its entirety.

BACKGROUND

The most widely used dosage forms for oral administration include tablets and capsules. However, such dosage forms have several disadvantages. For example, it is estimated that 50% of the population have problems swallowing tablets. In particular, it is difficult for some elderly persons to swallow tablets or capsules or to medicate children who are unable or unwilling to swallow tablets or capsules. This leads to poor or non-compliance with the treatment, and thus has a negative impact on the efficacy of the treatment. The bitter taste of many actives precludes the medication from being easily sprinkled onto food, a commonly used method of administering medications to elderly and children.

A number of methods are known for masking the taste of drugs; taste masking techniques may be divided into physical, chemical, biochemical and organoleptic methods. The technique to be adopted will depend on several factors, but primarily on the extent of bitterness of the drug to be incorporated into an oral pharmaceutical formulation. Organoleptic methods of taste-masking involve addition of a flavoring and/or sweetening agent and as such are relatively simple. However, simple addition of a taste-masking agent such as a flavoring agent or sweetener is frequently not useful by itself, unless the drug to be taste-masked is not particularly bitter. The most common masking methods, however, are based on physical means, including agglomeration, coating, and microencapsulation. Microencapsulation is essentially a process by which coatings are applied to small particles of solids, droplets of liquids or dispersions, so as to form microcapsules.

The taste masked formulation of bitter drug-containing cores should allow the complete release of the drugs in the gastrointestinal tract within a suitable time period. For example, bitter drug-containing cores incorporated into chewable tablets typically have thick coatings of mostly water-insoluble polymers, to resist fracture during tablet compression and/or during chewing and concomitant leakage of the bitter active; however, in this case a substantially complete release of the drug from such chewable tablets in the gastrointestinal tract may be achieved only after several hours from administration.

Among the drugs having a bitter taste there are the bisquinoline drugs. Bisquinoline derivatives are compounds with two quinoline groups bound by a covalent aliphatic or aromatic link. Several of these compounds have been identified as antimalarian medicaments and include hydroxypiperaquine, dichlorquinazine, 1,4-bis (7-chloro-4-quinolylamino) piperazine, piperaqine. Bisquinolines includes free form of the compound and their pharmaceutically acceptable different forms, such as salts, solvates, esters, racemic form, enantiomers, diastereomers, metabolites, prodrugs, analogues, polymorphs, hydrates, hyper-hydrate. Particularly interesting is piperaquine (PQ) and piperaquine tetraphosphate tetrahydrate phosphate (PQP). PQP is the bisquinoline, 4,4'-(1,3-propanediyldi-4,1-piperazinediyl) bis(7-chloroquinoline) phosphate hydrate (1:4:4) or 7-chloro-4-[4-[3-[4-(7-chloroquinolin-4-yl)piperazin-1-yl]propyl]piperazin-1-yl]quinoline phosphoric acid, hydrate. Its molecular formula is: $C_{29}H_{32}Cl_2N_6 \cdot 4(H_3PO_4) \cdot 4(H_2O)$, MW: 999.56. The molecular structure is:

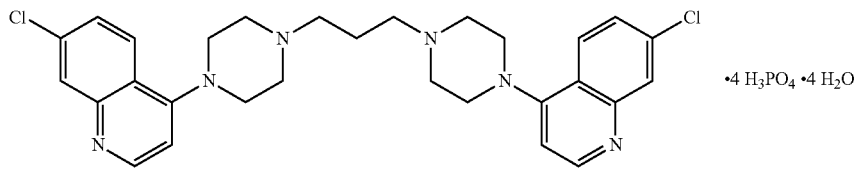 [SMILES: Clc1ccc2c(N3CCN(CCCN4CCN(c5ccnc6cc(Cl)ccc56)CC4)CC3)ccnc2c1]

Any crystalline polymorphs and hydrates of PQ and PQP representing different solid state molecular forms of the same compound can be used in the present invention.

Formulating piperaquine or piperaquine phosphate in their different forms is complicated by its bitter taste. Furthermore, PQP may induce chemical reactions on chemically reactive agents; instability and decomposition or degradation of chemically sensitive active agent such as dihydroartemisinin may occur when this agent is used in combination with PQP (Chem. Med. Chem., 2007, 1448-1463). Moreover, the formulation prepared with the bisquinoline drug should be controlled and customized both when PQP is used alone and in combination with other active agent(s).

SUMMARY OF THE INVENTION

The present invention provides a taste-masked microcapsule composition of a bisquinoline drug, wherein the microcapsule comprises a drug core and a coating (layer) of a polymeric material over the core and having the average coating weight of said microcapsule of from about 2 to about 40% weight of the total weight of the microcapsule composition.

Particularly interesting is coacervated microcapsule composition comprising piperaquine or piperaquine phosphate and their pharmaceutically acceptable different forms, such as salts, solvates, or prodrugs thereof. The invention provides the pharmaceutical compositions comprising these microcapsule compositions with suitable drug content combined with a taste masking effect. The pharmaceutical compositions may be also used to form a stable combination product (combo product) of PQP microcapsules with at least one unstable or chemically sensitive active agent. Chemically sensitive or reactive agent has high chemical reactivity, it contains reactive moiety/ies, such as for example acetal groups, and easily undergoes degradation reactions, such as hydrolysis or dehydrogenation to form for example aldehyde/ketone and ring opening degradation products.

The present invention also provides a process for preparing microcapsule composition of bisquinoline drug and the process for preparing pharmaceutical compositions comprising taste-masked microcapsule alone or in combination with other drug. The microcapsule preparation process includes the steps of: (a) forming a mixture comprising a bisquinoline drug, a polymeric material, and an organic solvent, (b) inducing the phase separation of the polymeric material from the solvent onto the drug, and (c) separating the drug microcapsule composition from the organic solvent.

Microencapsulation of bisquinoline drug (PQ or PQP) in the different forms is carried out to mask the bad taste, to minimize discoloration upon light exposure. The microencapsulation disclosed in the present invention is also effective in preventing and minimizing the degradation of further highly reactive agent induced by PQP, when both active agent and drug are formulated in a combo dosage form.

Figure 1:
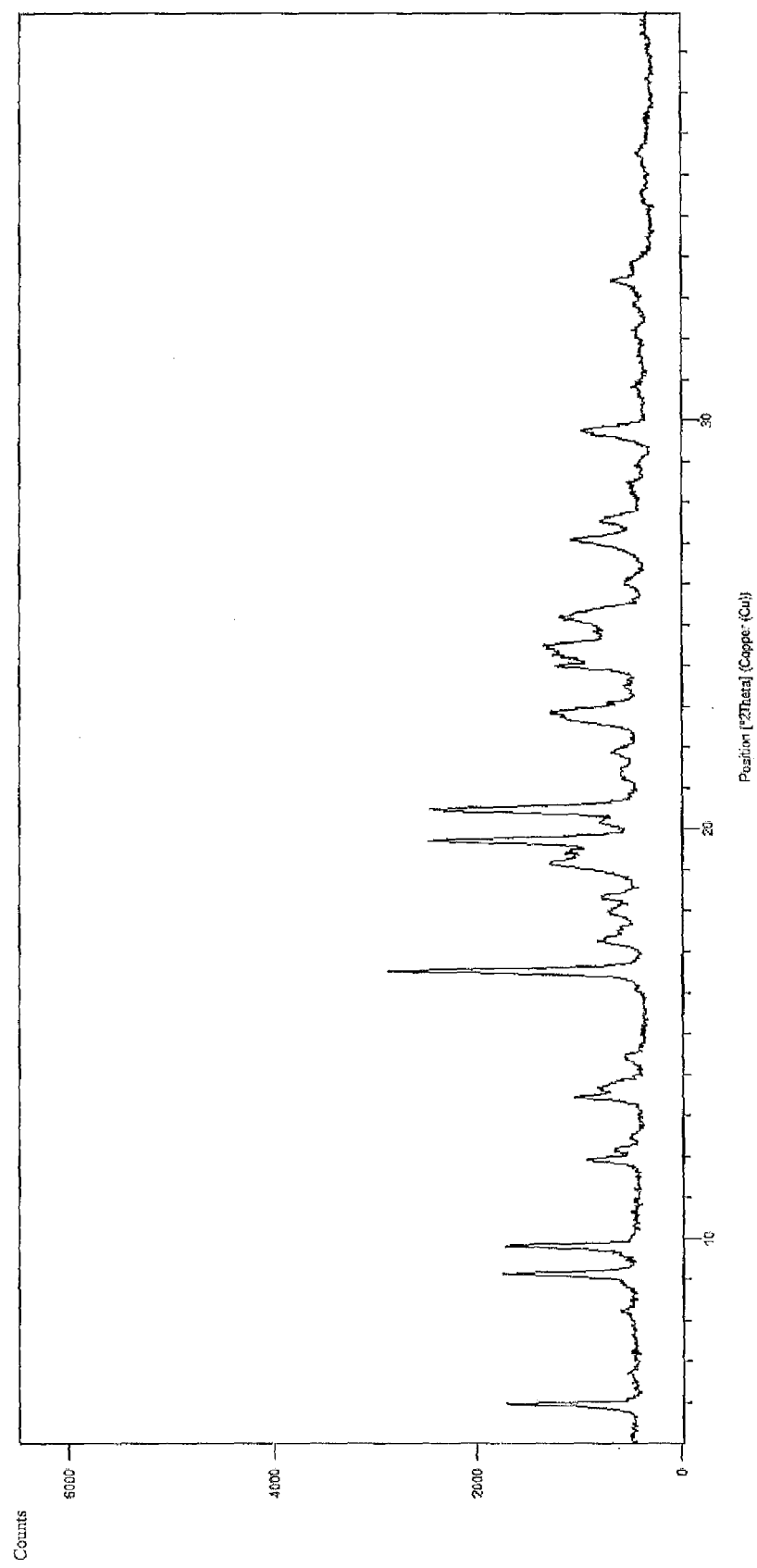
FIG. 1: XRPD of both PQP (top) and of PQP microcapsules of Sample 2 (bottom)
Figure 1:
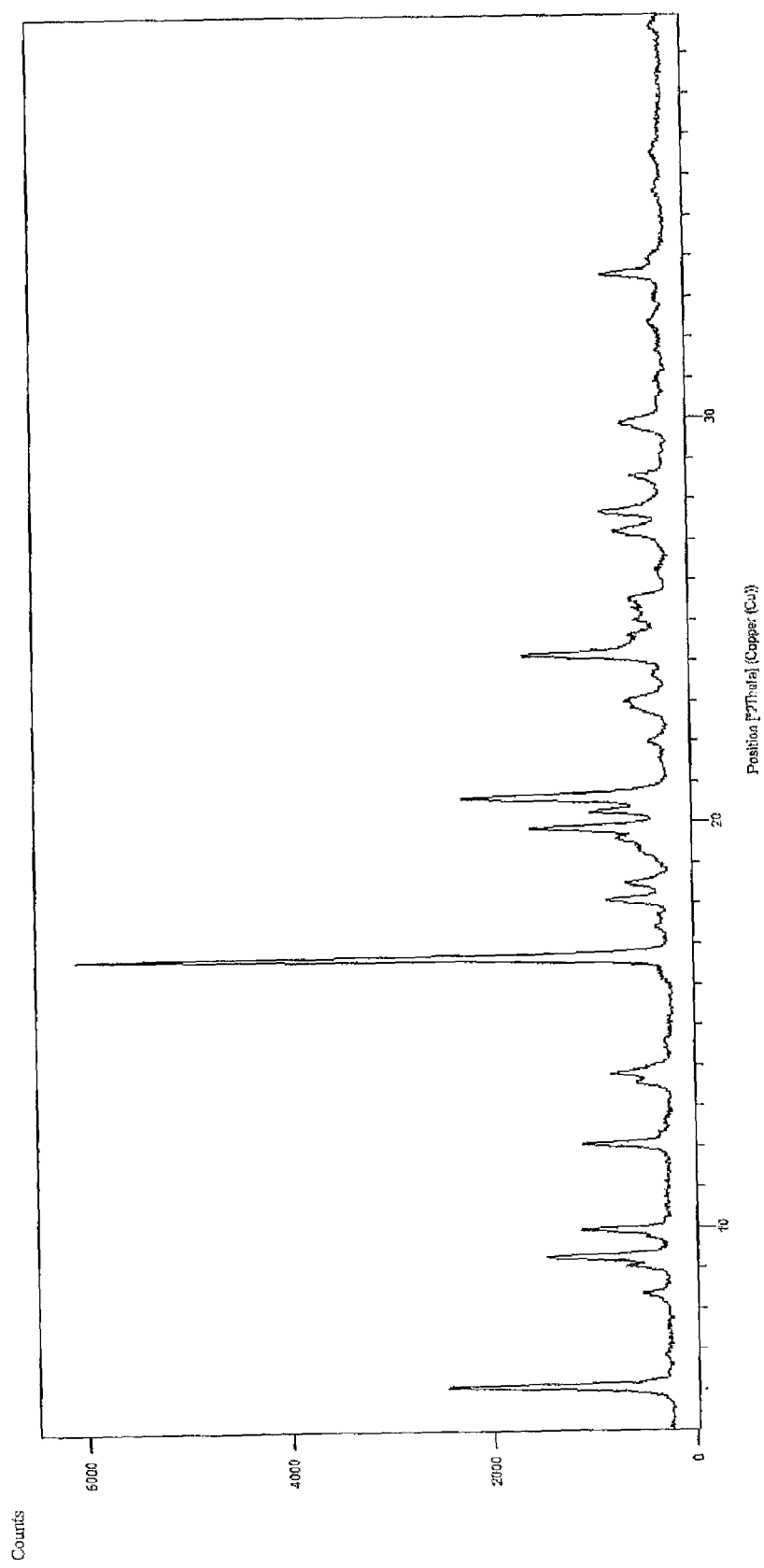

In all figures the "%" represents the bisquinoline fraction released with respect to the total amount.

DETAILED DESCRIPTION OF THE INVENTION

All documents cited herein are incorporated by reference for all purposes.

As used herein, the term "microcapsules" refers to a drug core coated with polymeric material, that is the polymeric material forms a layer around the drug core.

The term "coacervated microcapsules" refers to a drug core coated with polymeric material using the coacervation method.

"Microencapsulation conducted by phase separation" and "coacervation" mean an encapsulation process in which the drug is dispersed in a solution containing a coating polymeric material, and procedures are then followed which result in deposition of the coating on the drug core, thus preparing "coacervated microcapsules".

As used herein, the term "coating weight" or "coating level" refers to the dry weight of the polymeric material divided by the weight of the entire microcapsule, multiplied by 100. For example, a coating weight of 15% w/w means that for the given microcapsule, the coating constitutes 15% of the weight of the microcapsule. As used herein, the term "average coating weight" refers to the mean value of the coating weight for a population of microcapsules. For example, if half of the microcapsules in a given population have a coating weight of 10% w/w and the other half has a coating weight of 20% w/w, the average coating weight for the given population of microcapsules is 15% w/w. All "coating weight" or "coating level" values given in the present text are "average coating weight".

The term "pharmaceutical formulation" as used herein refers to formulations containing the microcapsules of the invention in combination with carriers or excipients suited to a selected drug delivery dosage form.

As used herein and unless otherwise specified, references to bisquinoline drug or piperaquine (PQ) or piperaquine phosphate (PQP) also encompasses a salt, solvate, or prodrug thereof; it is also intended for esters, racemic form, enantiomers, diastereomers, polymorphs, hydrates, or hyper-hydrate thereof.

The present invention provides a taste-masked microcapsules composition of bisquinoline drug, where the microcapsule consists of a drug core and a coating (also called coating layer) of a polymeric material and wherein the average coating weight of said microcapsule is from about 2 to about 40% weight of the total weight of the microcapsule composition. The bisquinoline drug is selected from the group consisting of such as hydroxypiperaquine, dichlorquinazine, 1,4-bis (7-chloro-4-quinolylamino) piperazine, piperaquine, piperaquine phosphate or pharmaceutically acceptable different forms, such as salts, solvates, hydrates, hyper-hydrate esters, metabolites, prodrugs, analogues, racemic form, enantiomers, diastereomers polymorphs thereof.

In one embodiment of the present invention, the bisquinoline drug is piperaquine phosphate in any pharmaceutically acceptable different form.

In one embodiment of the invention the bisquinoline is piperaquine tetraphosphate in hydrated form.

The coating of polymeric material of the present invention is deposited over the drug core thus forming an uniform layer over the core. The polymeric material may be any suitable, pharmaceutically acceptable polymer that forms a coating around the drug particles, and thereby yields drug microcapsules exhibiting taste-masked properties. Examples of polymers which may be used in the present invention are selected from the group consisting of ethylcellulose, polyvinyl acetate cellulose acetate, cellulose acetate butyrate, ammonium-methacrylate copolymers, cellulose acetate phthalate, cellulose acetate butyrate, polymethacrylates, hydroxypropyl methylcellulose phthalate, carboxymethyl ethylcellulose, polylactic acid and mixtures thereof. In the present invention the coating polymeric material is preferably insoluble in water.

In one embodiment, the water-insoluble polymeric material of the invention is ethylcellulose.

The amount and type of polymeric material in the coating contributes toward regulating the release of the drug and modulating the degree of taste masking. The average coating weight of the microcapsules of the present invention (also called coating level) is from about 2 to about 40% weight of the total weight of the microcapsule, or from about 5 to about 30% weight of the total weight of the microcapsule, or from about 10 to about 20% weight of the total weight of the microcapsule composition, including about 5% w/w, about 10% w/w, about 15% w/w, about 20% w/w, about 25% w/w, about 30% w/w, about 35% w/w, or about 40% w/w. The average coating weight of the microcapsules of the present invention is preferably from about 10% w/w to about 20% w/w. The microcapsules have an average coating weight of preferably about 10% w/w, or about 15% w/w, or about 20% w/w.

The wettability of the water insoluble polymeric coating of the microcapsules may be improved by treatment of the microcapsules with surfactants.

The taste masking of the coating is effective both on dry form and after suspension in water (60 seconds).

The microcapsules have particles size distribution (PDS) in the range comprised between 180 and 400 microns, preferably between 200 and 300 μm.

In one embodiment of the invention the taste-masked microcapsule composition consists of a drug core and a coating (layer) of a coacervated polymeric material.

In one embodiment of the invention the taste-masked microcapsule compositions consists of piperaquine tetraphosphate tetrahydrate (PQP.4H$_2$O) core and a coating (layer) of coacervated ethylcellulose.

In one embodiment of the invention the microcapsules of a bisquinoline (such as piperaquine tetraphosphate tetrahydrate) may be combined with additional active agent. The additional agent may be a drug that is not suitable to be used in pharmaceutical formulation because of its intrinsic chemical instability (such as agent sensitive to hydrolysis or that may undergo various degradation pathways) and/or also incompatible with many substances, including bisquinoline drugs (such as PQP).

The microcapsule of bisquinoline drug (such as PQ or PQP) or any of its forms is effective in:
- masking the unpleasant taste of the drug;
- preventing/minimizing discoloration of the drug induced by light exposure;
- preparing stable combination with other unstable or chemically reactive active agents by preventing and minimizing the degradation induced by PQP.

The characteristics of the produced microcapsules can be summarized:
- optimal "in vitro" dissolution profile;
- coating level uniform around the drug core and constant from batch to batch;
- drug stability upon storage;
- drug's (PQ or PQP) physical properties such as crystalline structure are maintained after microencapsulation process;
- light discoloration of the drug microencapsulated equivalent to that of starting drug;
- particles size distribution (PDS) in the range comprised between 180 and 400 microns, preferably between 200 and 300 μm;
- values of residual ingredients used in the preparation process (such as cyclohexane and phase inducer agent, PSI) always low and consistent with pharmaceutically allowable ranges.

The pharmaceutical compositions of the present invention may comprise taste-masked microcapsule composition of a bisquinoline drug and further inactive excipients.

In another embodiment, the present invention provides a process for microcapsules preparation.

The microcapsules of the present invention may be prepared by providing a homogeneous solution of a polymeric material in a suitable solvent in which the drug core and, optionally, coating additives are dispersed in suspension. Phase separation may then be applied to cause insolubilization of the polymeric material, which gels (coacervates) around the drug crystals to form the microcapsules. Phase separation may be performed, for example, through variation in temperature or in pH or by adding to the organic solvent a material promoting phase-separation (phase inducer agent) that cause the coacervation of the polymeric material. Finally, the microcapsules obtained are subjected to hardening, if required, and recovered.

More specifically, the microencapsulation process used for the preparation of taste-masked microcapsules of the present invention comprises the following steps: (a) forming a mixture comprising a bisquinoline drug, a polymeric material, and an organic solvent, (b) inducing the phase separation of the polymeric material from the solvent onto the drug, and (c) separating the drug microcapsule composition from the organic solvent.

In one embodiment the microencapsulation process comprises: (a) forming a mixture comprising a bisquinoline drug, a polymeric material, a material for promoting phase separation of the polymeric material, and an organic solvent, (b) inducing phase separation of the polymeric material from the solvent onto the drug, and (c) separating the drug microcapsules from said organic solvent.

Hence, the microcapsules of the bisquinoline drug of the invention are prepared by first forming a mixture of the bisquinoline drug, a polymeric material (to serve as the coating), and a material for promoting phase separation of the polymeric material (phase inducer agent) and optionally further ingredients in an organic solvent. Mixing is preferably conducted along with stirring or agitation using any number of conventional means. The solvent should be one in which the polymeric materials are soluble at higher temperatures, i.e., temperatures generally on the order of 70° C. or higher, but insoluble at ambient temperature; also, the drug should be substantially insoluble in the solvent at all temperatures used in the manufacturing process. After admixture of these initial components, the suspension so formed is heated for a time period and to a temperature sufficient to dissolve the first and second polymeric materials in the solvent. In addition, stirring is preferably continued at a predetermined stirring rate; a suitable stirring rate may be readily determined by one skilled in the art. The temperature is at or below the boiling point of the solvent; generally the components will be heated to a temperature of 70° C. or higher, and preferably to a temperature of at least about 75° C. However, care must be taken not to heat to a temperature which could degrade the drug. Phase separation of the polymeric material from the solvent onto the drug core is induced by cooling at appropriate rate and to appropriate temperature, thus producing a dispersion of the drug microcapsule (microencapsulated drug). It will be appreciated by those skilled in the art that the cooling rate can be varied to optimize properties of the microcapsules, e.g., with respect to aggregation, flowability and release profile. The solvent and phase inducer agent are then removed by decanting, filtering or the like, followed by washing with solvent to remove any traces of the phase inducer agent, and then drying, again at appropriate temperature so that the drug or coating material could be adversely affected. Drying is usually although not necessarily conducted for at least about 6 hours, and longer.

Suitable phase inducer agents which may be used in the present invention include polyethylene, polyisobutylene, butyl rubber, polybutadiene, isoprene methacrylic polymers, organosilicon polymers such as polydimethyl siloxane, paraffin, etc. In one embodiment, the phase inducer agent is polyethylene (epolene).

The organic solvent may be a single organic solvent or it may include a mixture of organic solvents. In accordance with the coacervation process, the organic solvent is chosen so as to dissolve the coating polymeric material, but not the drug and the possible coating additive(s) which remain dispersed in the form of solid particles in suspension.

Suitable organic solvents include cyclohexane or other hydrocarbon solvents. In one embodiment, the organic solvent is cyclohexane.

Suitable polymeric material include ethylcellulose, polyvinyl acetate, cellulose acetate, cellulose acetate butyrate, ammonium-methacrylate copolymers, cellulose acetate phthalate, cellulose acetate butyrate, polymethacrylates, hydroxypropyl methylcellulose phthalate, carboxymethyl ethylcellulose, polylactic acid and mixtures thereof.

The optionally further ingredients may be a gastrosoluble pore former; this ingredient may be a gastrosoluble organic or inorganic pore-formers and may be selected from the group consisting of calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate and mixtures thereof.

In one embodiment of the process for preparing taste-masked particles according to the present invention, the drug is piperaquine tetraphosphate tetrahydrate, the water-insoluble polymer is ethylcellulose, the phase inducer agent is polyethylene, the solvent is cyclohexane.

In one embodiment of the invention, the drug is piperaquine tetraphosphate tetrahydrate, the water-insoluble polymer is ethylcellulose in amount between about 1.2 and 2% w/w, the phase inducer agent is polyethylene in amount between about 0.5 and about 2% w/w, the solvent is cyclohexane.

In one embodiment of the invention, the drug is piperaquine tetraphosphate tetrahydrate, the water-insoluble polymer is ethylcellulose in amount of about 1.2% w/w, the phase inducer agent is polyethylene in amount of about 2% w/w, the solvent is cyclohexane.

In one embodiment of the invention, the drug is piperaquine tetraphosphate tetrahydrate, the water-insoluble polymer is ethylcellulose in amount of about 1.2% w/w, the phase inducer agent is polyethylene in amount of about 0.5% w/w, the solvent is cyclohexane.

In one embodiment of the invention, the drug is piperaquine tetraphosphate tetrahydrate, the water-insoluble polymer is ethylcellulose in amount of about 2% w/w, the phase inducer agent is polyethylene in amount of about 2% w/w, the solvent is cyclohexane.

The taste-masked composition of the invention may be also prepared by other methods. Core particles comprising a bisquinoline drug may be prepared followed by coating said core particles by applying a film forming polymer optionally in presence of other coating additives; this can be achieved for example by fluid bed. Said film forming polymer may be a single polymer or may be water-insoluble polymer in mixture with further ingredients, such as a gastrosoluble organic or inorganic pore-formers. The water-insoluble polymer may be selected from the group consisting of ethylcellulose, polyvinyl acetate, cellulose acetate, cellulose acetate butyrate, methacrylate copolymers and combinations thereof. The gastrosoluble pore former may be selected from the group consisting of calcium carbonate, calcium phosphate, calcium saccharide, calcium succinate, calcium tartrate, ferric acetate, ferric hydroxide, ferric phosphate, magnesium carbonate, magnesium citrate, magnesium hydroxide, magnesium phosphate and mixtures thereof.

In another embodiment, the taste-masked drug microcapsule, optionally combined with additional drug may be combined with inactive carrier or excipients. Excipients for use in the compositions or dosage forms of the present invention include fillers, diluents, glidants, disintegrants, binders, lubricants etc. Other pharmaceutically acceptable excipients include acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include, but are not limited to, lactose (e.g. spray-dried lactose, α-lactose, β-lactose, Tabletose®, various grades of Pharmatose®, Microtose® or Fast-Floc®), microcrystalline cellulose (e.g. Avicel PH101, Avicel PH102, Ceolus KG-802, Ceolus KG-1000, Prosolv SMCC 50 or SMCC90, various grades of Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylhydroxyethylcellulose and other cellulose derivatives, sucrose, xanthan gum, cyclodextrin (e.g., gamma-cyclodextrin), agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc. or combinations thereof.

Specific examples of diluents include. e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, xanthan gum, gamma-cyclodextrin, etc. and combinations thereof.

Specific examples of glidants and lubricants include, e.g., stearic acid, magnesium stearate, calcium stearate or other metallic stearates, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate, etc.

Other excipients include, e.g., flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Non-limiting examples of flavoring agents include, e.g., cherry, orange, banana, or other acceptable fruit flavors, or mixtures of cherry, orange, and other acceptable fruit flavors, at up to, for instance, about 3% based on the tablet weight. In addition, the compositions of the present invention can also include one or more sweeteners such as aspartame, sucralose, or other pharmaceutically acceptable sweeteners, or mixtures of such sweeteners, at up to about 2% by weight, based on the tablet weight. Furthermore, the compositions of the present invention can include one or more FD&C colorants at up to, for instance, 0.5% by weight, based on the tablet weight.

Antioxidants include, e.g., ascorbic acid, ascorbyl palmitate, butylated hydroxyanisole, butylated hydroxytoluene, hypophosphorous acid, monothioglycerol, potassium metabisulfite, propyl gallate, sodium formaldehyde sulfoxylate, sodium metabisulfite, sodium thiosulfate, sulfur dioxide, tocopherol, tocopherol acetate, tocopherol hemisuccinate, TPGS or other tocopherol derivatives, etc.

In another embodiment, the taste-masked microcapsules composition of the invention may be formulated into a variety of final dosage forms including free-flowing material, powder, granule, tablet, capsule or sachet.

Any further manipulation of the PQP microcapsule for the preparation of a dosage form may be carried out under controlled temperature and low moisture conditions. This approach may be used when the formulation includes some unstable or chemically reactive active agents. Controlled conditions that may be applied may include temperature below about 27° C. and relative humidity below about 50% RH.

Tablets may be in form of a chewable tablet or a dispersible tablet. Chewable tablets are solid dosage form containing the drug that is intended to be chewed, producing a residue in the oral cavity that is easily swallowed; it is therefore suitable also for administration to a patient (both adult and children) who may have swallowing difficulties. Dispersible tablets are solid dosage form that can be dispersed in small amount of liquid before administration giving a homogenous dispersion, or they can be easily dispersed directly in the mouth (orally dispersible tablets). Sachets may be prepared for permanent or extemporaneous suspensions and for direct administration in the mouth. The powder may be a fast dissolving powder that is formulated in a dry syrup for ease of swallowing; It may be administered directly in powder form, or first hydrated with a liquid, for example with 3-5 mL of water in a tablespoon or 15-50 mL of water in a glass.

The present invention discloses a process for preparing a tablet comprising: (a) forming a mixture comprising a bisquinoline drug, a coating polymeric material, a material for promoting phase separation of the polymer, and an organic solvent, (b) inducing phase separation of the polymeric material from the solvent onto the drug, (c) separating the drug microcapsules from said organic solvent, (d) mixing the drug microcapsules and other excipients to prepare a compressible blend, and (e) compressing said compressible blend into tablets. The process may further comprise adding at least one other active agent in step (d).

The microcapsules may be granulated before mixing them with other excipients or before mixing with other drug (step d); or the microcapsule may be mixed with the other active agent and then this mixture may be granulated and then mixed with other excipients. This granulation step may be also applied in the preparation of dosage forms different from the tablet.

The microcapsules of the invention or the final pharmaceutical composition comprising the drug microcapsules may further receive one or more further protective coating layers, such as HPMC, HPC, PVA and other water soluble polymers.

In another embodiment, the present invention provides a method for treating malaria. The method comprises administering to an individual in need thereof a pharmaceutical composition comprising taste-masked microcapsules, wherein the microcapsules comprise the drug and a water-insoluble polymer coating; the composition may further comprise an additional pharmaceutically effective agent, for example dihydroartemisinin. The dose of the microencapsulated drug alone or in combination with an additional pharmaceutically effective agent to be administered to an individual may vary depending on the age of the individual being treated as well as the indication. The following examples are provided for purposes of illustration, and should in no way be construed to limit the present invention.

EXPERIMENTAL

1. Methods for Characterization

Particle size distribution (PSD): an amount of microcapsules in the range of 25-50 g of microcapsules is poured into a 100 mL HDPE bottle, 0.2% (w/w) of Syloid 244 (colloidal silicon dioxide, WR Grace, Columbia, Md.) and manually blended for 2 minutes; the mixture of microcapsules and Syloid 244 is sieved then with a digital Octagon apparatus for 10 minutes at amplitude 7.

Bulk density and tapped density of powders is measured according to Method USP 34 <616>.

Dissolution profile: Ph Eur [2.9.3]; apparatus n° 2; dissolution medium: gastric simulated fluid pH 1.2 0.5% of Tween 80 without pepsin; dissolution medium volume: 900 mL; dissolution medium temperature: 37±0.5° C.; withdrawal at: 5, 15, 30, 60 and 120 min.

Water content: Karl Fischer titration: Ph. Eur. 2.5.12 Method; following sample titration conditions are applied: sample solvent: methanol: formamide 1:1; sample weight: 50 mg; the value of water content in a sample is expressed as % w/w.

Residual cyclohexane: gas-chromatography (head space analysis).

Photostability Testing: ICH conditions "Q1B: Photostability (Option 1)".

X-Ray Powder Diffraction (XRPD) measurements are performed on a Philips X'Pert PRO diffractometer (Bragg-Brentano geometry).

IR identity.

2. Piperaquine Microcapsules Prepared at Lab Scale 2.1. Method of Preparation

Cyclohexane is poured into the microencapsulation reactor. Then, under continuous stirring, piperaquine tetraphosphate tetrahydrate (PQP.4H$_2$O), ethylcellulose and polyethylene (epolene) are added. The mixture is heated and cooled down, microcapsules recovered, and then washed (one or more times), filtered, and dried overnight under static condition in an oven at about 40° C. The powder is sieved through a 500 μm opening stainless steel sieve.

TABLE 1

The Process flow sheet

| COMPONENTS | STEPS | EQUIPMENTS |
|---|---|---|
| Piperaquine<br>Ethylcellulose<br>Epolene[1]<br>Cyclohexane[2] | COACERVATION/PHASE SEPARATION | Reactor<br>Thermocryostate<br>Stirrer |
|  | WASHING<br>FILTERING<br>DRYING<br>SIEVING | Filtering system<br>Filtering system<br>Hood, Oven<br>Sieve |

[1]Removed during washing step;
[2]Removed during drying step

Different samples are prepared by using different amount of polymer ranging from 1.2 to 2% w/w (wherein 2% w/w means 20 g of ethylcellulose for 1 kg cyclohexane); different amount of epolene ranging from 0.5 to 2% w/w (wherein 2% w/w means 20 g of epolene for 1 kg cyclohexane); different samples of microcapsules with different amount of the ethylcellulose coating (coating level % w/w, where % w/w is the percentage of the polymer on the whole microcapsule weight) are prepared. The samples prepared are summarized in Table 2. Lab scale reactor (1 kg solvent) and industrial scale reactor (3 kg solvent) are used for the different preparations.

TABLE 2

Samples of piperaquine microcapsules

| Sample | Ethylcellulose % w/w | Epolene % w/w | Cyclohexane kg | Rpm | Coating level % w/w |
|---|---|---|---|---|---|
| 1 | 1.2 | 2 | 1 | 300 | 10 |
| 2 | 1.2 | 2 | 1 | 300 | 15 |
| 3 | 1.2 | 2 | 1 | 300 | 20 |
| 4 | 1.2 | 0.5 | 1 | 300 | 10 |
| 5 | 1.2 | 0.5 | 1 | 300 | 15 |
| 6 | 1.2 | 0.5 | 1 | 300 | 20 |
| 7 | 1.2 | 2 | 3 | 200 | 15 |
| 8, 9, 10 | 2 | 2 | 3 | 200 | 15 |
| 11 | 2 | 2 | 3 | 200 | 20 |
| 12 | 2 | 2 | 3 | 220 | 20 |
| 13, 14, 15, 16, 17, 18, 19 | 2 | 2 | 3 | 150 | 20 |
| 20 | 2 | 2 | 3 | 160 | 15 |

The microcapsules are characterized by appearance, particle size distribution, residual solvent content and dissolution rate. Microscopic evaluation at the end of the microencapsulation process of the samples showed appropriate uniform polymer coating deposition around the piperaquine particles consistent with the amount of the polymer used.

The amount of residual solvent (cyclohexane) is always below 100 ppm for all preparation of microcapsules prepared.

2.2. Compatibility of Piperaquine with the Coacervation Process Conditions

A compatibility study is carried out on piperaquine to assess the compatibility of the drug with the coacervation process. In particular, piperaquine undergoes heating/cooling cycles mimicking thermal excursions of the process. Then, the following tests are performed both before and after thermal cycles to ascertain the stability of piperaquine: water content analysis (Karl Fisher test); effect of mechanical stress; crystalline structure by XRPD. The results are summarized in the following Table 3.

| Test | $PQP \cdot 4H_2O$ before thermal cycle | $PQP \cdot 4H_2O$ after thermal cycle |
|---|---|---|
| Assay (%) ($PQP \cdot 4H_2O$) | 99.9 | 99.9 |
| Water content (%) | 8.9 | 8.5 |

The crystalline structure of piperaquine and that of the microcapsules of the Sample 2 are measured by XRPD and compared (FIG. 1): the process does not affect the crystalline structure of the $PQP.4H_2O$, since no change in the crystalline structure is recorded. The analysis confirms that the $PQP.4H_2O$ is not affected by heating/cooling cycle.

2.3. Particle Size Distribution

The PSD for the different samples is measured and reported in Table 4; all the samples match the 180-400 µm range. It is clear that the change of the coating level and the application of different process conditions do not significantly affect the PSD of the microcapsules.

TABLE 4

Particle size distribution of microcapsules with coating level (C.L.) 10, 15, 20% w/w

| | Ethylcellulose 1.2%/Epolene 2% | | | Ethylcellulose 1.2%/Epolene 0.5% | | |
|---|---|---|---|---|---|---|
| Sieve (µm) | C.L. 10% Sample 1 | C.L. 15% Sample 2 | C.L. 20% Sample 3 | C.L. 10% Sample 4 | C.L. 15% Sample 5 | C.L. 20% Sample 6 |
| >500 | 0.4 | 1.5 | 0.5 | 0.6 | 1.0 | 1.5 |
| >425 | — | 3.5 | 2.9 | — | 4.0 | 4.0 |
| >355 | 9.9 | 9.7 | 9.6 | 10.7 | 8.0 | 10.4 |
| >250 | 34.8 | 37.0 | 41.1 | 18.0 | 39.8 | 33.7 |
| >180 | 39.3 | 39.3 | 37.8 | 27.3 | 38.8 | 37.1 |
| >125 | 14.8 | 8.2 | 6.7 | 34.1 | 8.5 | 10.9 |
| <125 | 0.8 | 0.8 | 1.4 | 9.3 | 0.0 | 2.5 |
| 125-425 | — | 94.2 | 95.2 | — | 95.1 | 92.1 |
| 125-355 | 98.8 | — | — | 90.1 | — | — |

PSD is measured on microcapsules with 15% w/w coating level produced at different scale and processing conditions (Table 5); Sample 8 is measured on 3 replicates thus showing that the reproducibility of the process is high.

TABLE 5

PSD of microcapsules with coating level 15% w/w

| PDS (sieves) Sieve µm | % fraction (w/w) | | | |
|---|---|---|---|---|
| | Sample 2 | Sample 7 | Sample 8 (n = 3) | SD |
| >500 | 1.5 | 1.5 | 0.5 | 0.12 |
| >425 | 3.5 | 2.5 | 4.1 | 0.46 |
| >355 | 9.7 | 10.5 | 13.9 | 1.10 |

TABLE 5-continued

PSD of microcapsules with coating level 15% w/w

| PDS (sieves) Sieve μm | % fraction (w/w) | | | |
|---|---|---|---|---|
| | Sample 2 | Sample 7 | Sample 8 (n = 3) | SD |
| >250 | 37.0 | 56.0 | 43.9 | 0.58 |
| >180 | 39.3 | 27.5 | 26.4 | 0.72 |
| >125 | 8.2 | 2.0 | 9.3 | 0.46 |
| <125 | 0.8 | 0.0 | 1.9 | 0.42 |

As shown in Table 6 the PSD is within the 180-400 μm range for all the batches manufactured at large scale and having coating level 20% w/w.

TABLE 6

PSD of microcapsules with coating level 20% w/w

| PSD (sieves) Sieve μm | % fraction (w/w) | | | |
|---|---|---|---|---|
| | Sample 3 | Sample 11 | Sample 12 | Sample 13 |
| >500 | 0.5 | 0.8 | 0.0 | 0.0 |
| >425 | 2.9 | 1.6 | 0.8 | 3.2 |
| >355 | 9.6 | 6.5 | 5.2 | 23.2 |
| >250 | 41.1 | 20.1 | 26.4 | 52.4 |
| >180 | 37.8 | 26.6 | 42.8 | 18.8 |
| >125 | 6.7 | 25.8 | 21.6 | 2.0 |
| <125 | 1.4 | 18.4 | 3.2 | 0.4 |

2.4. Photostability Test

Piperaquine microcapsules are tested for their photostability; the tested samples have coating level 10% and 20% w/w and are prepared both with ethylcellulose 1.2% w/w and epolene 2.0% w/w and with ethylcellulose 1.2% w/w and epolene 0.5% w/w. The test is carried out by comparing the microcapsules versus the piperaquine alone. The samples do not show differences in discoloration upon light exposure.

2.5. Dissolution, Assay and Water Content of Microcapsules

Figure 2:
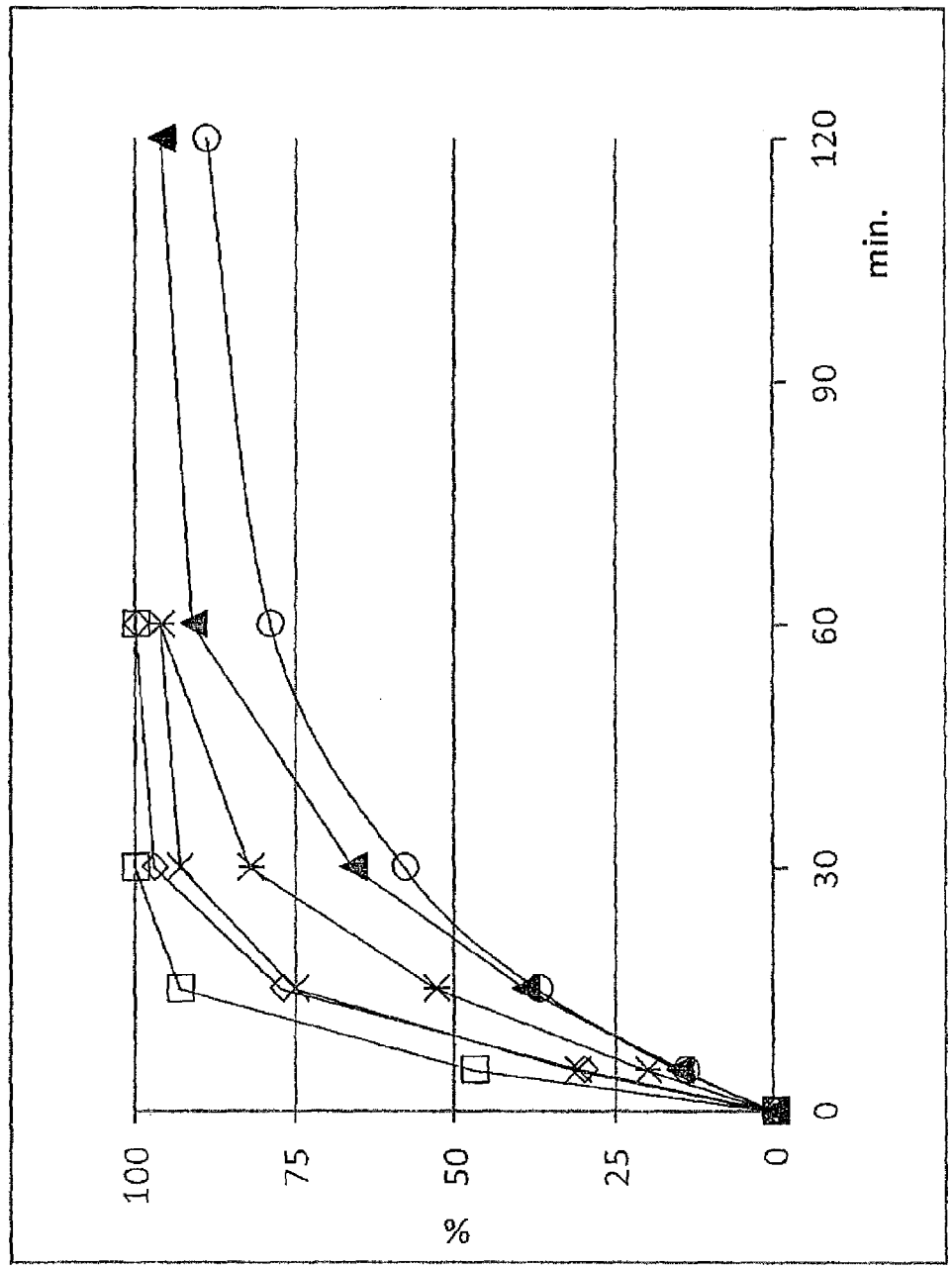
FIG. 2: "In vitro" dissolution profiles of microcapsules with coating level 10, 15, 20% w/w; □: Sample 1; ◇: Sample 2; ▲: Sample 3; x: Sample 4; *: Sample 5; ○: Sample 6

The results of the "in vitro" dissolution test (DRT) of microcapsules are summarized in Table 7 and presented as a graph in FIG. 2.

TABLE 7

Analysis of microcapsules with coating level 10, 15, 20% w/w

| | Ethylcellulose 1.2%/Epolene 2% 1 kg Cyclohexane, HC 300 rpm | | | | | | Ethylcellulose 1.2%/Epolene 0.5% 1 kg Cyclohexane, HC 300 rpm | | | | | |
|---|---|---|---|---|---|---|---|---|---|---|---|---|
| | C.L. 10% Sample 1 | | C.L. 15% Sample 2 | | C.L. 20% Sample 3 | | C.L. 10% Sample 4 | | C.L. 15% Sample 5 | | C.L. 20% Sample 6 | |
| DRT (min) | % | SD | % | SD | % | SD | % | SD | % | SD | % | SD |
| 5 | 47 | 4 | 30 | 1 | 15 | 1 | 31 | 3 | 20 | 1 | 14 | 0 |
| 15 | 93 | 2 | 77 | 3 | 39 | 1 | 75 | 3 | 53 | 1 | 37 | 0 |
| 30 | 100 | 1 | 97 | 2 | 66 | 1 | 93 | 2 | 82 | 1 | 58 | 1 |
| 60 | 100 | 1 | 100 | 1 | 91 | 3 | 96 | 2 | 96 | 2 | 79 | 1 |
| 120 | — | — | — | — | 96 | 3 | — | — | — | — | 89 | 1 |
| Assay (%) (PQP•4H$_2$O) | 100.2 | | 100.4 | | 100.7 | | 100.6 | | 100.4 | | 101.3 | |
| Water content (%) | 7.6 | | 7.3 | | 7.2 | | 7.7 | | 7.2 | | 7.1 | |

By analyzing the data there is a clear evidence of the high coating efficiency of the coacervation system applied. With regards to Karl Fischer data, it is observed that the loss of water is very limited (above 7% referred to the drug only and not to the microcapsules); this behavior is important because it shows that no change in crystalline structure occurs during processing. In fact, when an excessive water loss occurs than this may induce a change of the crystalline structure of the drug, i.e. from crystalline to amorphous.

Figure 3:
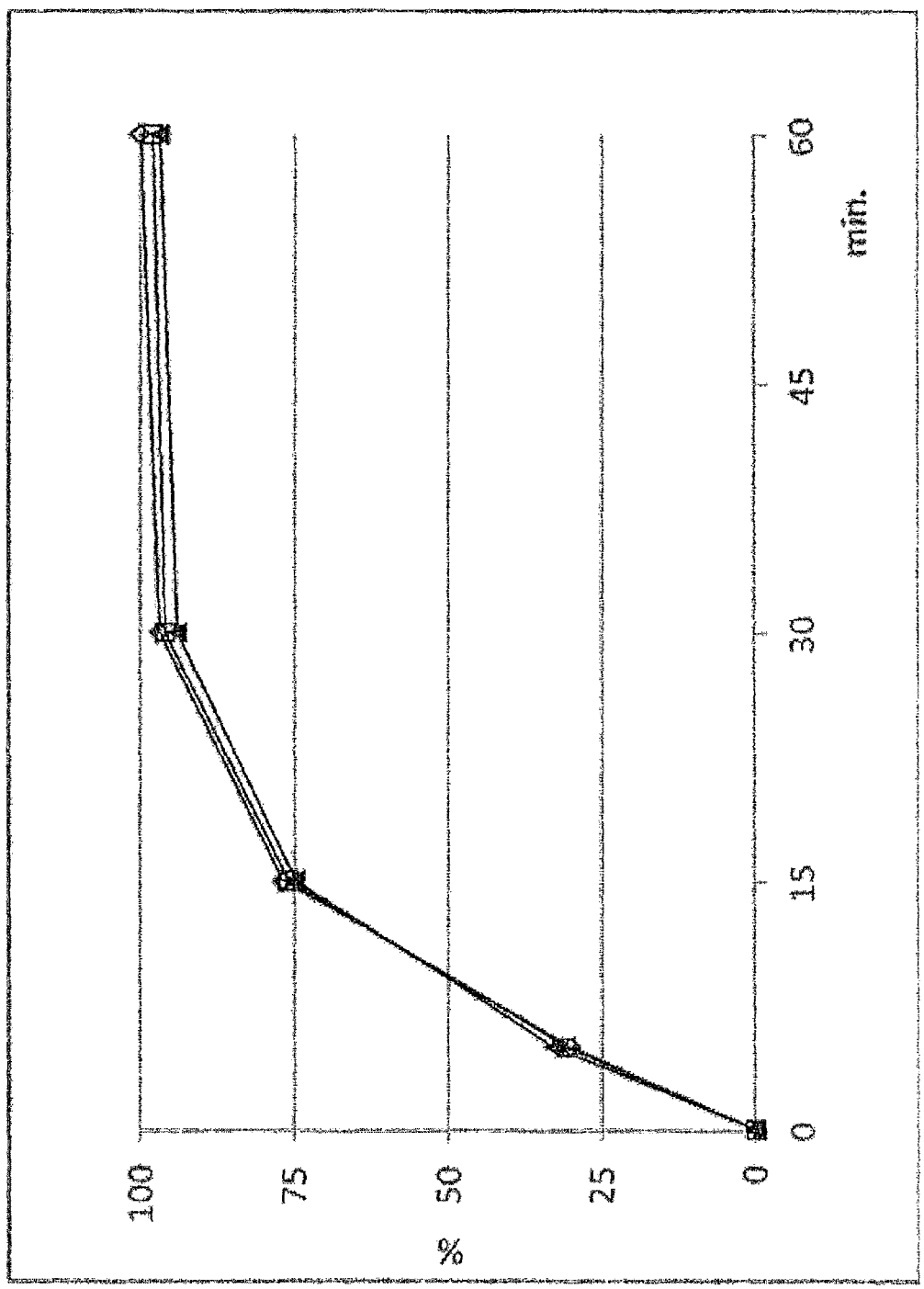
FIG. 3: "In vitro" dissolution profiles of microcapsules with coating level 15% w/w; ◇: Sample 2; □: Sample 7; ▲: Sample 8

Table 8 and FIG. 3 show that the 15% coating level microcapsules produced at different scale and different processing condition behaves similarly in term of DRT, PSD, coating efficiency. The level of reproducibility is high.

TABLE 8

Analysis of microcapsules with coating level of 15% w/w

| | Coating level 15% | | |
|---|---|---|---|
| | EC 1.2% EP 2% | | EC 2% EP 2% |
| | Sample 2 1 kg | Sample 7 3 kg | Sample 8 3 kg |
| DRT (min) (n = 3) | % SD | % SD | % SD |
| 5 | 30  1 | 31  1 | 33  1 |
| 15 | 77  3 | 76  1 | 75  2 |
| 30 | 97  2 | 96  1 | 94  3 |
| 60 | 100  1 | 98  1 | 97  3 |
| Assay (%) (PQP•4H$_2$O) | 100.4 | 100.2 | 100.3 |
| Water content (%) | 7.3 | 7.0 | 7.4 |
| Cyclohexane (ppm) | NA | NA | 18 |

Figure 4:
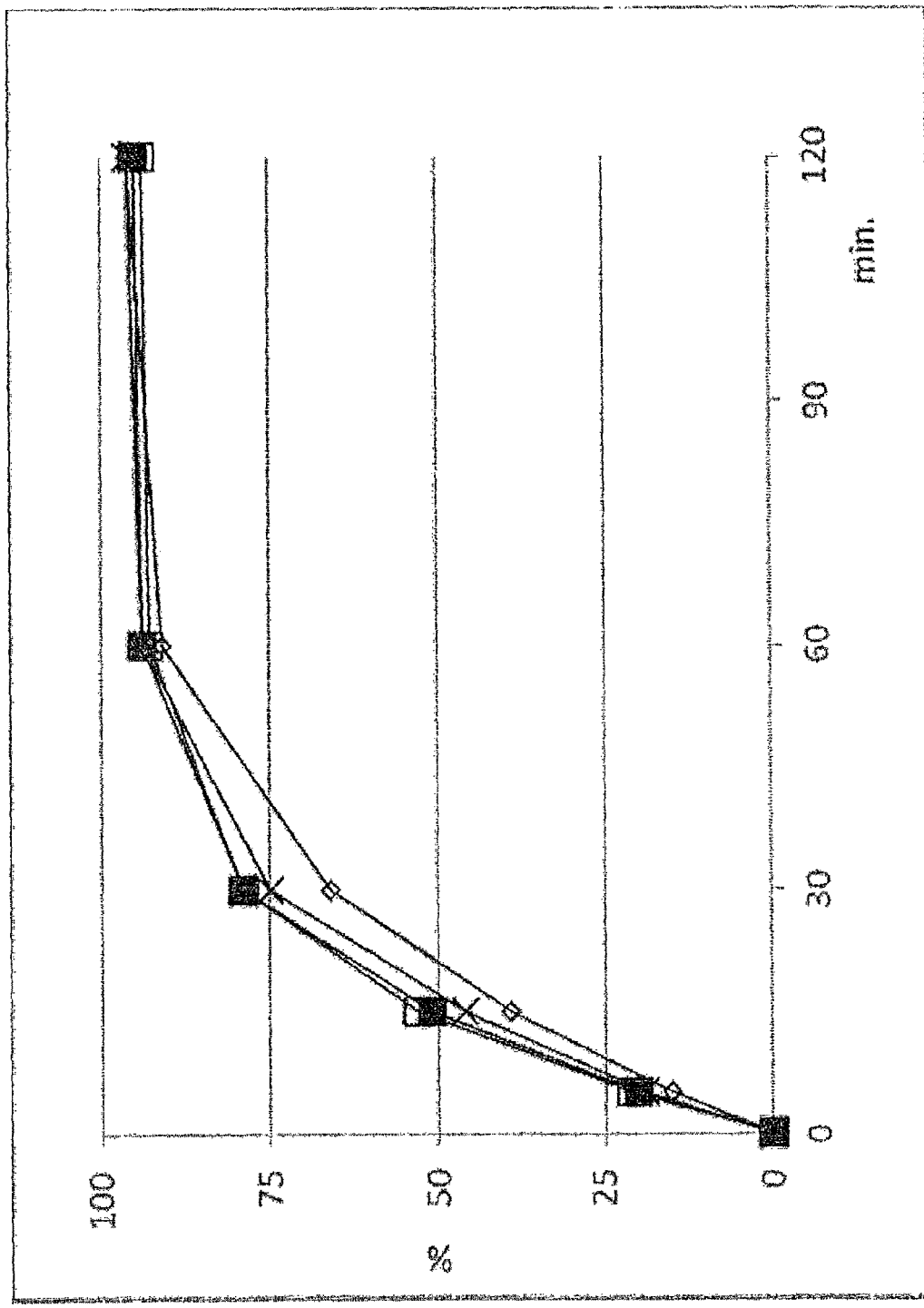
FIG. 4: "In vitro" dissolution profiles of microcapsules with coating level 20% w/w; ▲: Sample 3; □: Sample 11; ■: Sample 12; x: Sample 13

Dissolution data and profile shown in Table 9 and FIG. 4 refers to the microcapsules with coating level 20% w/w produced by scaling up the process.

TABLE 9

Analysis of microcapsules with coating level 20% w/w

| | Coating level 20% w/w | | | |
|---|---|---|---|---|
| | EC 1.2% EP 2% | EC 2%/EP 2% | | |
| | Sample 3 1 kg 300 rpm | Sample 11 3 kg 200 rpm | Sample 12 3 kg 200 rpm | Sample 13 3 kg 150 rpm |
| DRT (min) (n = 3) | % SD | % SD | % SD | % SD |
| 5 | 15  1 | 21  1 | 20  1 | 19  1 |
| 15 | 39  1 | 53  1 | 51  3 | 46  0 |
| 30 | 66  1 | 79  1 | 79  2 | 75  1 |
| 60 | 91  3 | 93  2 | 94  1 | 94  2 |
| 120 | 96  3 | 94  2 | 95  1 | 96  2 |
| Assay (%) (PQP•4H$_2$O) | 100.7 | 101.1 | 101.0 | 100.4 |
| Water content (%) | 7.2 | 6.4 | 6.4 | 6.4 |

Figure 5:
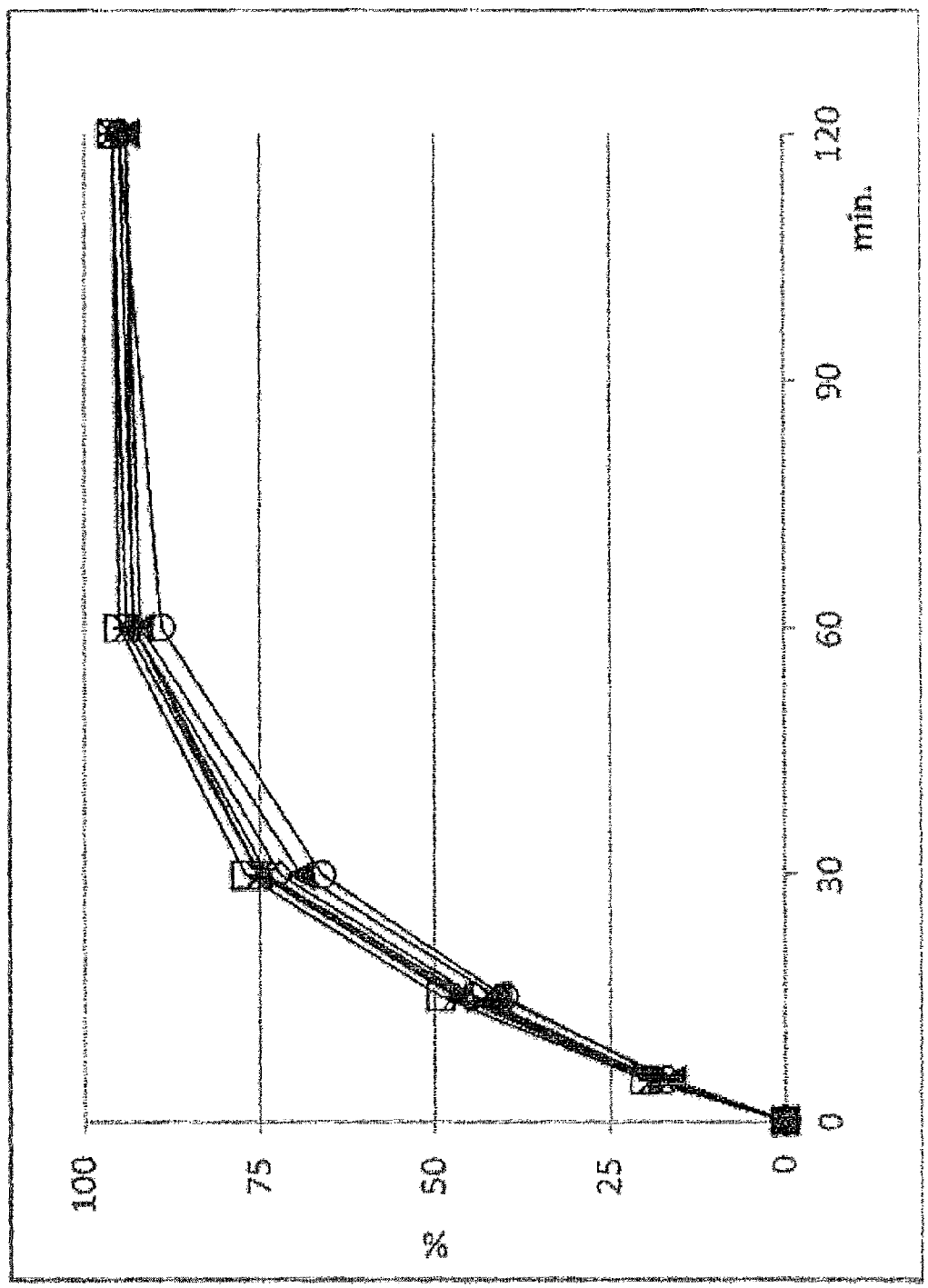
FIG. 5: "In vitro" dissolution profiles of microcapsules with 20% w/w coating level; x: Sample 13; ○: Sample 14; –: Sample 15; ▲: Sample 16; +: Sample 17; ◇: Sample 18; □: Sample 19; *: Sample 21

Table 10 and FIG. 5 show the results of the characterization of sub-batches with coating level 20% w/w regarding the dissolution profile, the PSD and the assay and the results of "in vitro" dissolution profile, assay, PSD KF analysis, residual cyclohexane and residual epolene for final mixture (Sample 21=Sample 13+Sample 14+Sample 15+Sample 16+Sample 17+Sample 18+Sample 19).

TABLE 10

Analysis of microcapsules with 20% w/w coating level

| | EC 2%/EP 2% - 150 rpm - 3 kg Reactor | | | | | | | |
|---|---|---|---|---|---|---|---|---|
| DRT (min) | Sample 13 | Sample 14 | Sample 15 | Sample 16 | Sample 17 | Sample 18 | Sample 19 | Sample 21 n = 6 |
| (n = 3) | % SD | % SD | % SD | % SD | % SD | % SD | % SD | % SD |
| 5 | 19  1 | 17  1 | 19  1 | 16  1 | 19  1 | 18  1 | 20  1 | 19  1 |
| 15 | 46  0 | 40  1 | 45  2 | 41  2 | 47  1 | 44  2 | 49  1 | 47  2 |
| 30 | 75  1 | 66  1 | 74  2 | 69  1 | 75  1 | 72  3 | 77  2 | 75  2 |
| 60 | 94  2 | 89  1 | 93  2 | 92  0 | 93  1 | 93  3 | 95  1 | 94  2 |
| 120 | 96  2 | 95  1 | 95  2 | 94  1 | 94  2 | 95  2 | 96  2 | 96  1 |
| Assay (%) (PQP•4H$_2$O) | 100.4 | NA | NA | NA | NA | NA | NA | 100.0 |
| Water content (%) | 6.4 | NA | NA | NA | NA | NA | NA | 6.2 |
| Epolene (% w/w) | NA | NA | NA | NA | NA | NA | NA | 0.3 |
| Cyclohexane (ppm) | NA | NA | NA | NA | NA | NA | NA | 45 |
| Sieve μm | PSD fraction (% w/w) | | | | | | | |
| >500 | 0.0 | 0.0 | 0.0 | 0.0 | 0.0 | 0.0 | 0.0 | 0.2 |
| >425 | 3.2 | 2.5 | 4.8 | 4.4 | 3.3 | 3.5 | 2.1 | 4.4 |
| >355 | 23.2 | 19.2 | 17.0 | 25.6 | 22.3 | 21.1 | 19.5 | 18.4 |
| >250 | 52.4 | 48.1 | 52.2 | 46.8 | 50.5 | 44.8 | 46.4 | 52.0 |
| >180 | 18.8 | 24.1 | 19.5 | 17.8 | 16.3 | 20.1 | 21.9 | 20.0 |
| >125 | 2.0 | 5.1 | 4.7 | 4.5 | 6.0 | 8.6 | 9.3 | 4.0 |

TABLE 10-continued

Analysis of microcapsules with 20% w/w coating level

EC 2%/EP 2% - 150 rpm - 3 kg Reactor

| DRT (min) | Sample 13 | | Sample 14 | | Sample 15 | | Sample 16 | | Sample 17 | | Sample 18 | | Sample 19 | | Sample 21 n = 6 | |
|---|---|---|---|---|---|---|---|---|---|---|---|---|---|---|---|---|
| (n = 3) | % | SD | % | SD | % | SD | % | SD | % | SD | % | SD | % | SD | % | SD |
| <125 | 0.4 | | 1 | | 1.8 | | 0.9 | | 1.6 | | 2 | | 0.8 | | 1.0 | |
| 125-425 | 96.4 | | 96.5 | | 93.4 | | 94.7 | | 95.1 | | 94.6 | | 97.1 | | 94.4 | |
| Bulk density-Tapped density (g/mL) | NA | | NA | | NA | | NA | | NA | | NA | | NA | | 0.58-0.63 | |

Figure 6:
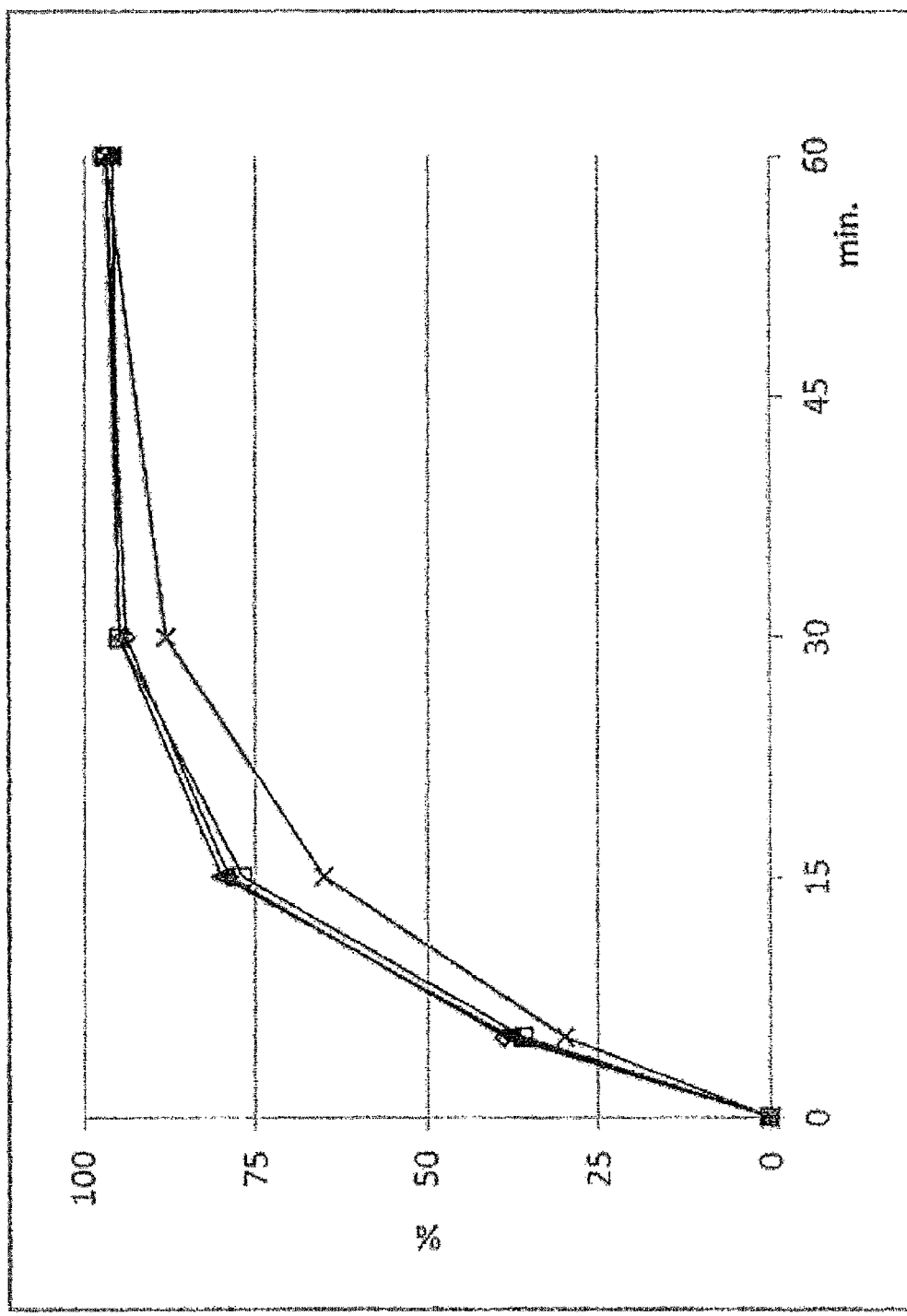
FIG. 6: "In vitro" dissolution profiles of microcapsules with 15% w/w of coating level; ◇: Sample 9; □: Sample 10; ▲: Sample 22; x: Sample 20.

Table 11 and FIG. 6 show the results of in-vitro dissolution of the manufactured sub-batches with coating level 15% w/w.

TABLE 11

Analysis of microcapsules with 15% w/w of coating level
(Sample 22 = Sample 9 + Sample 10)

| | Coating Level 15% | | | | | | | |
|---|---|---|---|---|---|---|---|---|
| | EC 2% EP 2% 3 kg solvent | | | | EC 2% EP 2% 2 kg solvent | | | |
| | Sample 9 | | Sample 10 | | Sample 22 n = 6 | | Sample 20 | |
| DRT (min) (n = 3) | % | SD | % | SD | % | SD | % | SD |
| 5 | 39 | 2 | 36 | 2 | 38 | 1 | 30 | 1 |
| 15 | 79 | 2 | 77 | 0 | 80 | 1 | 65 | 2 |
| 30 | 94 | 1 | 95 | 1 | 95 | 1 | 88 | 1 |
| 60 | 97 | 1 | 97 | 1 | 96 | 1 | 97 | 1 |
| Theoretical assay (PQP•4H$_2$O) | 850.0 mg/g | | | | | | | |
| Assay (%) (PQP•4H$_2$O) | NA | | NA | | 100.6 | | 100.4 | |
| Water content (%) | NA | | NA | | 7.0 | | 6.3 | |
| Epolene (% w/w) | NA | | NA | | 0.3 | | NA | |
| Cyclohexane (ppm) | NA | | NA | | 50 | | 40 | |

| PSD (sieve) | PDS fraction (% w/w) | | | |
|---|---|---|---|---|
| >500 µm | 0.3 | 0.6 | 0.7 | 0.9 |
| >425 µm | 3.7 | 3.9 | 3.9 | 4.6 |
| >355 µm | 13.1 | 13.5 | 13.4 | 14.5 |
| >250 µm | 45.3 | 45.9 | 44.8 | 47.7 |
| >180 µm | 27.7 | 26.9 | 26.7 | 25.7 |
| >125 µm | 8.5 | 8.0 | 8.8 | 6.3 |
| <125 µm | 1.4 | 1.2 | 1.7 | 0.3 |
| 125-425 µm | 94.6 | 94.3 | 93.7 | 94.2 |

3. Piperaquine Microcapsules Prepared at Industrial Scale

3.1. Method of Preparation

Piperaquine tetraphosphate tetrahydrate, excipients and cyclohexane are placed into the 80 gallons reactor. The reactor paddle speed is set and the thermal cycle of microencapsulation begins; the temperature parameters of the cycle are set (maximum heating temperature 80° C.). Drugs, polymeric material, phase separation inducing agent and solvent are loaded in amount as reported in Table 12.

TABLE 12

| Components of microcapsules | | |
|---|---|---|
| Components | Amount (kg) | Material Concentration (% w/w) |
| PQP•4H$_2$O | 20.0 | 7.2 |
| Ethylcellulose | 5.0 | 1.8 |
| Polyethylene | 5.0 | 1.8 |
| Cyclohexane | 248.0 | 89.2 |
| Total | 278.0 | 100.0 |

At the end of the thermal cycle. the paddle rotation is stopped and the product settled down. The supernatant (solvent and polyethylene excipient) is removed using a pump and fresh solvent is added (about 120 kg). The agitation is restarted for short period of time and then the microcapsules are filtered under vacuum in a fluid bed equipped with a 70 µm stainless steel sieve on the bottom. The whole process and the filtration as well is carried out in inert nitrogen atmosphere. After the solvent removal by filtration, the microcapsules are dried up to the level of the residual cyclohexane of below 3880 ppm. The obtained product is discharged and sieved trough a 600 µm stainless steel sieve.

A set of coacervation processes are performed (Table 13), wherein a different stirrer speed is applied: about 100 rpm (Sample 23, Sample 24, Sample 25) and or about 65-70 rpm (Sample 26, Sample 27, Sample 28, Sample 29).

TABLE 13

Coacervation process conditions

| Microcapsule batch | Sample 23 | Sample 24 | Sample 25 | Sample 26 | Sample 27 | Sample 28 | Sample 29 |
|---|---|---|---|---|---|---|---|
| Cyclohexane fresh/distilled (kg) | 248.0 | NA | 248.0 | 248.0 | 248.0 | 248.0 | NA |
| Cyclohexane media (kg) | NA | 128.8 | NA | NA | NA | NA | 136.0 |
| Cyclohexane filtered (kg) | NA | 119.2 | NA | NA | NA | NA | 112.0 |
| PQP•4H$_2$O (kg) | 20.0 | 20.0 | 20.0 | 20.0 | 20.0 | 20.0 | 20.0 |
| Ethylcellulose (kg) | 5.00 | 5.00 | 5.00 | 5.00 | 5.00 | 5.00 | 5.00 |
| Epolene (kg) | 5.00 | 1.50 | 5.00 | 5.00 | 5.00 | 5.00 | 1.20 |

Table 14 reports the compositions and the process parameters used for the preparation of the large scale batches. All the batches are produced applying a coating level of ethylcellulose equal to 20% w/w.

TABLE 14

Large scale microcapsule batches: composition and process parameters

| Microcapsule batch | Sample 30 | Sample 31 | Sample 32 | Sample 33 | Sample 34 | Sample 35 |
|---|---|---|---|---|---|---|
| Cyclohexane fresh/distilled (kg) | 248.0 | NA | 248.0 | NA | NA | NA |
| Cyclohexane media (kg) | NA | 142 | NA | 248 | 248 | 248 |
| Cyclohexane filtered (kg) | NA | 106 | NA | | | |
| PQP•4H$_2$O (kg) | 20.0 | 20.0 | 20.0 | 20.0 | 20.0 | 20.0 |
| Ethylcellulose (kg) | 5.00 | 5.00 | 5.00 | 5.00 | 5.00 | 5.00 |
| Epolene (kg) | 5.00 | 1.20 | 5.00 | 1.20 | 1.20 | 1.20 |
| Sedimentation Time (min) | 5 | 5 | 5 | 5 | 5 | 5 |
| Supernatant removed (kg) | 136.0 | 136.0 | 136.0 | 136.0 | 136.0 | 136.0 |
| Fresh cyclohexane for filtration (kg) | 120 | 120 | 120 | 120 | 120 | 120 |
| Filtration time (min) | 7 | 7 | 7 | 7 | 7 | 7 |
| Paddle (rpm) | 65-70 | 65-70 | 65-70 | 65-70 | 65-70 | 65-70 |

The batches are then mixed in a 120 L bin for 15 minutes at 10 rpm. Table 15 reports the composition of the microcapsules mixtures.

TABLE 15

Composition of microcapsules mixtures

| Final mix batch | Sample 30 (kg) | Sample 31 (kg) | Sample 32 (kg) | Sample 33 (kg) | Sample 34 (kg) | Sample 35 (kg) | Total (kg) |
|---|---|---|---|---|---|---|---|
| Sample 36 (kg) | 23.1 | 23.3 | — | — | — | — | 46.4 |
| Sample 37 (kg) | — | — | 23.7 | 23.3 | — | — | 47.0 |
| Sample 38 (kg) | — | — | — | — | 23.2 | 23.2 | 46.4 |

3.2. Particle Size Distribution of Microcapsules Prepared at Industrial Scale

Analysis is performed on 25 g up to 50 g on stainless steel sieves. Table 16 and 17 report the results for the different batches.

TABLE 16

Particle size distribution

| PSD | Sample 23 | Sample 24 | Sample 25 | Sample 26 | Sample 27 | Sample 28 | Sample 29 |
|---|---|---|---|---|---|---|---|
| >500 μm | 0.4 | 2.2 | 1.3 | 1.2 | 5.3 | 3.4 | 1.2 |
| >425 μm | 4.2 | 1.6 | 2.3 | 1.6 | 4.8 | 1.5 | 1.4 |
| >355 μm | 16.9 | 4.4 | 5.0 | 7.4 | 8.5 | 5.4 | 4.4 |
| >250 μm | 50.4 | 19.0 | 17.2 | 22.6 | 28.7 | 25.2 | 39.7 |
| >180 μm | 19.4 | 38.3 | 30.6 | 36.0 | 34.1 | 39 | 36.7 |
| >125 μm | 5.4 | 27.2 | 32.3 | 25.6 | 15.7 | 20.9 | 14.6 |
| <125 μm | 3.3 | 7.3 | 11.3 | 5.6 | 2.9 | 4.6 | 2 |
| 125-425 μm | 92.1 | 88.9 | 85.1 | 91.6 | 91.8 | 90.5 | 95.4 |

TABLE 17

Particle size distribution

| PSD | Sample 30 | Sample 31 | Sample 32 | Sample 33 | Sample 34 | Sample 35 |
|---|---|---|---|---|---|---|
| >500 μm | 3 | 3 | 1 | 1 | 1 | 1 |
| >425 μm | 3 | 3 | 1 | 1 | 1 | 1 |
| >355 μm | 7 | 7 | 17 | 18 | 11 | 13 |
| >250 μm | 36 | 31 | 27 | 25 | 24 | 21 |
| >180 μm | 35 | 37 | 41 | 44 | 50 | 47 |
| >125 μm | 13 | 16 | 12 | 7 | 11 | 13 |
| <125 μm | 2 | 3 | 1 | 4 | 2 | 3 |
| 125-425 μm | 94 | 94 | 98 | 95 | 97 | 95 |

3.3. Characterization of Microcapsules Prepared at Industrial Scale

Different tests have been carried out in order to characterize of microcapsules. Tables 18 and 19 report the results.

TABLE 18

Analysis of piperaquine microcapsules (industrial scale)

| Microcapsule batch | Time (min) | Sample 23 % | SD | Sample 24 % | SD | Sample 25 % | SD | Sample 26 % | SD | Sample 27 % | SD | Sample 28 % | SD | Sample 29 % | SD |
|---|---|---|---|---|---|---|---|---|---|---|---|---|---|---|---|
| DRT in buffer: pH 1.2 GF + 0.5% of Tween 80, 900 ml; paddle: 50 rpm; 37.0 ± 0.5° C. | 5 | 19 | 0.9 | 37 | 0.5 | 31 | 0.5 | 23 | 0.5 | 26 | 0.5 | 23 | 1.0 | 22 | 1.5 |
| | 15 | 49 | 0.8 | 81 | 2.1 | 71 | 4.2 | 56 | 0.8 | 64 | 0.8 | 57 | 1.2 | 54 | 2.6 |
| | 30 | 77 | 1.2 | 98 | 1.4 | 91 | 1.5 | 83 | 0.8 | 90 | 0.5 | 85 | 1.6 | 84 | 1.2 |
| | 60 | 94 | 1.6 | 99 | 1.3 | 98 | 1.6 | 96 | 0.8 | 97 | 0.5 | 96 | 1.3 | 96 | 0.6 |
| | 120 | 97 | 1.5 | 99 | 1.2 | 98 | 1.6 | 98 | 1.0 | 97 | 0.4 | 97 | 1.6 | 97 | 0.6 |
| Theoretical assay (PQP•4H$_2$O) | | 800 mg/g | | | | | | | | | | | | | |
| Assay (%) (PQP•4H$_2$O) | | 100.8 | | 100.5 | | 100.5 | | 100.2 | | 99.8 | | 99.9 | | 99.4 | |
| Water content (%) | | 5.1 | | 5.5 | | 5.7 | | 5.6 | | 5.0 | | 5.6 | | 5.7 | |
| Residual cyclohexane (ppm) (spec ≤3880 ppm) | | 1498 | | 1946 | | 1095 | | 598 | | 1297 | | 1107 | | 1656 | |
| Residual epolene (% w/w) (spec ≤1.5%) | | 0.3 | | 0.1 | | 0.4 | | 0.9 | | 0.7 | | 0.3 | | 0.6 | |
| Bulk density (g/mL) | | 0.56 | | nd | | nd | | nd | | nd | | nd | | nd | |
| Tapped density (g/mL) | | 0.60 | | nd | | nd | | nd | | nd | | nd | | nd | |
| Process yield (%) | | 75 | | 89 | | 90 | | 93 | | 93 | | 93 | | 94 | |

TABLE 19

Analysis of piperaquine microcapsules (industrial scale)

| Microcapsule batch | Time (min) | Specs (reference value) | Sample 30 % | SD | Sample 31 % | SD | Sample 32 % | SD | Sample 33 % | SD | Sample 34 % | SD | Sample 35 % | SD |
|---|---|---|---|---|---|---|---|---|---|---|---|---|---|---|
| DRT in buffer: pH 1.2 GF + 0.5% of Tween 80, 900 ml; paddle: 50 rpm; 37.0 ± 0.5° C. | 5 | — | 23 | 0.4 | 28 | 1.2 | 26 | 1.1 | 31 | 1.6 | 30 | 2.6 | 36 | 1.6 |
| | 15 | | 56 | 0.8 | 65 | 1.6 | 64 | 1.6 | 73 | 1.4 | 68 | 2.3 | 78 | 1.8 |
| | 30 | | 83 | 0.4 | 89 | 0.9 | 90 | 1.5 | 94 | 0.8 | 91 | 1.4 | 95 | 1.0 |
| | 60 | ≥70% | 97 | 0.0 | 97 | 0.8 | 98 | 1.5 | 97 | 1.2 | 96 | 1.5 | 97 | 0.4 |
| | 120 | — | 98 | 0.5 | 97 | 0.5 | 98 | 1.5 | 97 | 1.2 | 96 | 1.0 | 97 | 0.5 |

TABLE 19-continued

Analysis of piperaquine microcapsules (industrial scale)

| Microcapsule batch | Specs | Sample 30 | | Sample 31 | | Sample 32 | | Sample 33 | | Sample 34 | | Sample 35 | |
|---|---|---|---|---|---|---|---|---|---|---|---|---|---|
| Time (min) | (reference value) | % | SD | % | SD | % | SD | % | SD | % | SD | % | SD |
| Assay % (PQP) | 70-78% | 74 | | 75 | | nd | | nd | | nd | | nd | |
| Water content (%) | — | 5.9 | | 6.2 | | nd | | nd | | nd | | nd | |
| Residual cyclohexane (ppm) | ≤3380 ppm | 1385 | | 2508 | | 2009 | | 1210 | | 1658 | | 1806 | |
| Residual epolene (% w/w/) | ≤1.5% | 0.7 | | 0.9 | | 0.6 | | 0.2 | | 0.5 | | 0.3 | |
| Process yield (%) | | 92 | | 93 | | 95 | | 93 | | 93 | | 93 | |

4. Piperaquine Microcapsules Prepared at Industrial Scale for Registration Purposes (Sample 36, Sample 37) and for Clinical Trials (Sample 38)

4.1. Method of Preparation

Piperaquine tetraphosphate tetrahydrate, excipients and cyclohexane are placed into the 80 gallons reactor. The reactor paddle speed is set and the thermal cycle of microencapsulation begins; the temperature parameters of the cycle are set (maximum heating temperature 80° C.). Drugs, polymeric material, phase separation inducing agent and solvent are loaded in amount as reported in Table 20.

TABLE 20

Components of microcapsules

| Components | Amount (kg) | Material Concentration (% w/w) |
|---|---|---|
| PQP•4H$_2$O | 20 | 7.2 |
| Ethylcellulose | 5 | 1.8 |
| Polyethylene | 5 | 1.8 |
| Cyclohexane | 248 | 89.2 |
| Total | 278 | 100.0 |

At the end of the thermal cycle, the paddle rotation is stopped and the product settled down. The supernatant (solvent and polyethylene) is removed using a pump and fresh solvent is added (about 120 kg). The agitation is restarted for short period of time and then the microcapsules are filtered under vacuum in a fluid bed equipped with a 70 µm stainless steel sieve on the bottom. The whole process, and the filtration as well, is carried out in inert nitrogen atmosphere. After the solvent removal by filtration, the microcapsules are dried up to remove residual cyclohexane. The obtained product is discharged and sieved trough a 600 µm stainless steel sieve.

Coacervation process conditions are reported in Table 21.

TABLE 21

Coacervation process conditions

| | Sample 36 | | Sample 37 | | Sample 38 | |
|---|---|---|---|---|---|---|
| Drying (min) | 60 | 60 | 60 | 60 | 63 | 60 |
| Stirrer speed (rpm) | 70 | 70 | 70 | 70 | 70 | 70 |

TABLE 21-continued

Coacervation process conditions

| | Sample 36 | | Sample 37 | | Sample 38 | |
|---|---|---|---|---|---|---|
| Cyclohexane (fresh/distilled) (litres) | 310 | 0 | 0 | 0 | 310 | 0 |
| Cyclohexane media and filtered (litres) | 0 | 310 | 310 | 310 | 0 | 310 |
| Cyclohexane for washing step (litres) | 150 | 150 | 150 | 150 | 150 | 150 |
| PQP•4H$_2$O (kg) | 20 | 20 | 20 | 20 | 20 | 20 |
| Ethylcellulose (kg) | 5 | 5 | 5 | 5 | 5 | 5 |
| Epolene (kg) | 5 | 1.2 | 1.2 | 1.2 | 5 | 1.2 |

All the batches are produced by applying a coating level of ethylcellulose equal to 20% w/w.

4.2. Stability Testing of Batches Prepared for Registration and Clinical Trials

Sample 36, Sample 37, Sample 38 are packaged in double polyethylene bag (inner transparent bag, outer black bag). Stability of these batches has been evaluated at accelerated conditions (40° C./75% RH) for a period of 6 months, as well as at long-term stability conditions (25° C./60% RH) for a period of 12 months. Results shows that these samples are stable at all conditions tested (Tables 22-27). The assay, dissolution (DRT), residual water content (%) at all stability conditions are also comparable to the initial values of piperaquine microcapsules. Not more than 5% w/w of total related substances (decomposed PQP) are formed upon storage for 6 months at 40° C./75% RH for 6 months or at 25° C./60% RH for 12 months.

TABLE 22

Stability data for PQP microcapsules of Sample 36, conditions: 25° C. at 60% relative humidity

| Test | Specs | Time: 0 | time: 3 mo | time: 6 mo | time: 9 mo | time: 12 mo |
|---|---|---|---|---|---|---|
| Assay (%) (PQP) | 70-78% | 74 | 74 | 74 | 73 | 74 |
| Assay (%) (PQP) with respect to time: 0 | 95-105% | NA | 100 | 100 | 99 | 100 |

| Dissolution (min) (n = 6) | | % | DS | % | DS | % | DS | % | DS | % | DS |
|---|---|---|---|---|---|---|---|---|---|---|---|
| 5 | — | 31 | 2.1 | 30 | 1.5 | 29 | 0.8 | 28 | 1.0 | 27 | 0.8 |
| 15 | — | 69 | 1.2 | 70 | 1.5 | 68 | 1.2 | 68 | 1.3 | 65 | 1.0 |
| 30 | — | 92 | 0.8 | 92 | 0.8 | 92 | 0.0 | 92 | 0.5 | 90 | 2.3 |
| 60 | ≥70% | 98 | 0.5 | 97 | 0.4 | 98 | 0.5 | 98 | 0.0 | 97 | 0.8 |
| 120 | — | 98 | 0.5 | 97 | 0.4 | 98 | 0.4 | 98 | 0.4 | 98 | 1.0 |
| Water content (%) | — | 6.1 | | 6.3 | | 6.4 | | 6.7 | | 6.9 | |

TABLE 23

Stability data for piperaquine microcapsules of Sample 36, conditions: 40° C. at 75% relative humidity

| Test | Specs | Time: 0 | time: 3 mo | time: 6 mo |
|---|---|---|---|---|
| Assay (%) (PQP) | 70-78% | 74 | 74 | 74 |
| Assay (%) (PQP) with respect to time: 0 | 95-105% | NA | 100 | 100 |

| Dissolution (min) n = 6 | | % | DS | % | DS | % | DS |
|---|---|---|---|---|---|---|---|
| 5 | — | 31 | 2.1 | 28 | 1.0 | 29 | 1.3 |
| 15 | — | 69 | 1.2 | 68 | 1.5 | 69 | 2.4 |
| 30 | — | 92 | 0.8 | 91 | 1.0 | 92 | 0.4 |
| 60 | ≥70% | 98 | 0.5 | 97 | 0.5 | 98 | 0.4 |
| 120 | — | 98 | 0.5 | 98 | 0.5 | 98 | 0.4 |
| Water content (%) | — | 6.1 | | 6.4 | | 6.6 | |

TABLE 24

Stability data for piperaquine microcapsules of Sample 37, conditions: 25° C. at 60% relative humidity

| Test | Specs | Time. 0 | time: 3 mo | time: 6 mo | time: 9 mo | time: 12 mo |
|---|---|---|---|---|---|---|
| Assay (%) (PQP) | 70%-78% | 74 | 74 | 73 | 73 | 73 |
| Assay (%) (PQP) with respect to time = 0 | 95-105% | NA | 100 | 99 | 99 | 99 |

| Dissolution (min) (n = 6) | | % | DS | % | DS | % | DS | % | DS | % | DS |
|---|---|---|---|---|---|---|---|---|---|---|---|
| 5 | — | 33 | 1.5 | 32 | 1.5 | 33 | 1.2 | 33 | 0.8 | 30 | 1.2 |
| 15 | — | 72 | 1.0 | 72 | 2.3 | 75 | 1.8 | 74 | 0.5 | 70 | 1.6 |
| 30 | — | 93 | 0.5 | 93 | 0.9 | 94 | 0.8 | 94 | 0.8 | 93 | 0.4 |
| 60 | ≥70% | 97 | 0.8 | 97 | 0.5 | 98 | 1.0 | 98 | 0.5 | 98 | 0.0 |
| 120 | — | 97 | 0.8 | 98 | 0.5 | 98 | 0.6 | 97 | 0.8 | 98 | 0.4 |
| Water content (%) | — | 5.9 | | 6.4 | | 6.4 | | 7.0 | | 6.9 | |

TABLE 25

Stability data for piperaquine microcapsules batch Sample 37, conditions: 40° C. at 75% relative humidity

| Test | Specs | Time: 0 | time: 3 mo | time: 6 mo |
|---|---|---|---|---|
| Assay (%) (PQP) | 70-78% | 74 | 74 | 73 |
| Assay (%) (PQP) with respect to time: 0 | 95-105% | NA | 100 | 99 |

| Dissolution (min) (n = 6) | | % | DS | % | DS | % | DS |
|---|---|---|---|---|---|---|---|
| 5 | — | 33 | 1.5 | 34 | 0.5 | 33 | 1.0 |
| 15 | — | 72 | 1.0 | 74 | 1.7 | 75 | 0.6 |
| 30 | — | 93 | 0.5 | 94 | 0.5 | 94 | 0.4 |
| 60 | ≥70% | 97 | 0.8 | 97 | 0.8 | 97 | 0.0 |
| 120 | — | 97 | 0.8 | 97 | 0.4 | 97 | 0.0 |
| Water content (%) | — | 5.9 | | 6.3 | | 6.4 | |

TABLE 26

Stability data for piperaquine microcapsules of Sample 38, conditions: 25° C. at 60% relative humidity

| Test | Specs | Time: 0 | time: 3 mo | time: 6 mo | time: 9 mo | time: 12 mo |
|---|---|---|---|---|---|---|
| Assay (%) (PQP) | 70-78% | 74 | 73 | 74 | 74 | 73 |
| Assay (%) (PQP) with respect to time: 0 | 95-105% | NA | 99 | 100 | 100 | 99 |

| Dissolution (min) (n = 6) | | % | DS | % | DS | % | DS | % | DS | % | DS |
|---|---|---|---|---|---|---|---|---|---|---|---|
| 5 | — | 25 | 0.9 | 26 | 0.8 | 25 | 1.0 | 26 | 0.4 | 27 | 0.8 |
| 15 | — | 59 | 1.1 | 61 | 1.0 | 60 | 1.5 | 61 | 1.3 | 64 | 1.3 |
| 30 | — | 86 | 0.5 | 88 | 0.8 | 86 | 1.5 | 87 | 1.0 | 89 | 0.6 |
| 60 | ≥70% | 97 | 0.8 | 98 | 0.5 | 97 | 0.8 | 96 | 0.8 | 98 | 0.4 |
| 120 | — | 98 | 1.0 | 98 | 0.5 | 98 | 0.4 | 97 | 0.5 | 99 | 0.5 |
| Water content (%) | — | 5.9 | | 6.4 | | 6.8 | | 6.9 | | 7.4 | |

TABLE 27

Stability data for piperaquine microcapsules of Sample 38, conditions: 40° C. at 75% relative humidity

| Test | Specs | time: 0 | time: 3 mo | time: 6 mo |
|---|---|---|---|---|
| Assay (%) (PQP) | 70-78% | 74 | 73 | 74 |
| Assay (%) (PQP) with respect to time: 0 | 95-105% | NA | 99 | 100 |

| Dissolution (min) (n = 6) | | % | DS | % | DS | % | DS |
|---|---|---|---|---|---|---|
| 5 | | 25 | 0.9 | 26 | 0.8 | 26 | 1.2 |
| 15 | | 59 | 1.1 | 60 | 0.8 | 61 | 0.8 |
| 30 | | 86 | 0.5 | 87 | 1.0 | 87 | 0.8 |
| 60 | ≥70% | 97 | 0.8 | 97 | 1.3 | 97 | 0.0 |
| 120 | — | 98 | 1.0 | 98 | 1.0 | 98 | 0.4 |
| Water content (%) | | 5.9 | | 6.8 | | 6.9 | |

The invention claimed is:

1. A taste-masked microcapsule pharmaceutical composition of a bisquinoline drug, wherein the microcapsule comprises a drug core of a pharmaceutically effective amount of a bisquinoline drug and a coating over the core of a polymeric material, and having an average weight of the coating of said microcapsule of from about 2 to about 40% weight of the total weight of the microcapsule composition, wherein at least about 58% of the bisquinoline drug is released from the microcapsule composition within about 30 minutes when tested using the Ph. Eur. [2.9.3] dissolution test.

2. The composition of claim 1, wherein the bisquinoline is selected from the group consisting of hydroxypiperaquine, dichlorquinazine, 1,4-bis (7-chloro-4-quinolylamino) piperazine, and piperaquine (or a salt, solvate, or prodrug thereof.

3. The composition of claim 2, wherein the bisquinoline is piperaquine tetraphosphate tetrahydrate.

4. The composition of claim 1, wherein the polymeric material is selected from the group consisting of ethylcellulose, polyvinyl acetate, cellulose acetate, cellulose acetate butyrate, ammonium-methacrylate copolymers, cellulose acetate phthalate, cellulose acetate butyrate, polymethacrylates, hydroxypropyl methylcellulose phthalate, carboxymethyl ethylcellulose, polylactic acid and mixtures thereof.

5. The composition of claim 1, wherein the polymeric material is water insoluble.

6. The composition of claim 1, wherein the coating is deposited by coacervation.

7. The composition of claim 1, wherein the polymeric material is ethylcellulose.

8. The composition of claim 1, wherein the average weight of the coating of said microcapsule is from about 5 to about 30% weight of the total weight of the microcapsule composition.

9. The composition of claim 1, wherein the average weight of the coating of said microcapsule is from about 10 to about 20% weight of the total weight of the microcapsule composition.

10. The composition of claim 1, in combination with another active agent.

11. The composition of claim 10, wherein the other active agent is chemically sensitive.

12. The composition of claim 1, in a form of a free-flowing material, of a powder, tablet, capsule or sachet.

13. The composition of claim 12, wherein the tablet is chewable or orally dispersible tablet.

14. A process for preparing the composition of claim 1, comprising: (a) forming a mixture comprising a drug core of a pharmaceutically effective amount of a bisquinoline drug, a polymeric material, and an organic solvent, (b) inducing the phase separation of the polymeric material from the solvent onto the drug, and (c) separating the composition from the organic solvent.

15. The process of claim 14, wherein step (a) further comprises a material for promoting phase separation of the polymeric material.

16. The process of claim 14 or 15, wherein the polymeric material is selected from the group consisting of ethylcellulose, polyvinyl acetate, cellulose acetate, cellulose acetate butyrate, ammonium-methacrylate copolymers, cellulose acetate phthalate, cellulose acetate butyrate, polymethacrylates, hydroxypropyl methylcellulose phthalate, carboxymethyl ethylcellulose, polylactic acid and mixtures thereof.

17. The process of claim 16, wherein the polymeric material is ethylcellulose.

18. The process of claim 15, wherein material for promoting phase separation is selected from the group consisting of polyethylene, polyisobutylene, butyl rubber, polybutadiene, organosilicon polymer, and paraffin.

19. The process of claim 18, wherein the material is polyethylene.

20. The process of claim 14, wherein the bisquinoline drug is piperaquine tetraphosphate tetrahydrate.

21. The process of claim 14, further comprising steps: (d) mixing the separated composition and at least one other excipient to prepare a compressible blend and (e) compressing said compressible blend into tablets.

22. The process of claim 21, wherein the polymeric material is ethylcellulose.

23. The process of claim 21 or 22 further comprising adding in step (d) at least one other chemically sensitive active agent.

24. The composition of claim 1, wherein at least about 82% of the bisquinoline drug is released from the microcapsule composition within about 30 minutes when tested using the Ph. Eur. [2.9.3] dissolution test.

25. The composition of claim 1, wherein at least about 93% of the bisquinoline drug is released from the microcapsule composition within about 30 minutes when tested using the Ph. Eur. [2.9.3] dissolution test.

26. The composition of claim 1, wherein about 100% of the bisquinoline drug is released from the microcapsule composition within about 30 minutes when tested using the Ph. Eur. [2.9.3] dissolution test.

27. The composition of claim 1, wherein the average weight of the coating of said microcapsule is from about 5 to about 30% weight of the total weight of the microcapsule composition.

28. The composition of claim 1, wherein the average weight of the coating of said microcapsule is from about 10 to about 20% weight of the total weight of the microcapsule composition.

* * * * *